(12) United States Patent
Kinmon

(10) Patent No.: US 7,921,490 B2
(45) Date of Patent: Apr. 12, 2011

(54) PATIENT SUPPORT DEVICE AND METHOD FOR USE

(76) Inventor: Trip Kinmon, O'Fallon, MO (US)

(*) Notice: Subject to any disclaimer, the term of this patent is extended or adjusted under 35 U.S.C. 154(b) by 0 days.

(21) Appl. No.: 12/326,983

(22) Filed: Dec. 3, 2008

(65) Prior Publication Data
US 2009/0158526 A1 Jun. 25, 2009

Related U.S. Application Data

(60) Provisional application No. 61/015,437, filed on Dec. 20, 2007.

(51) Int. Cl.
*A61G 13/12* (2006.01)
(52) U.S. Cl. .................................. 5/621; 5/601
(58) Field of Classification Search .............. 5/621–624, 5/601, 600, 630, 632
See application file for complete search history.

(56) References Cited

U.S. PATENT DOCUMENTS

| | | | |
|---|---|---|---|
| 2,666,309 A * | 1/1954 | Anderson et al. | 15/257.7 |
| 2,910,259 A * | 10/1959 | Johnson | 248/118 |
| 4,109,338 A * | 8/1978 | Mertes | 15/105 |
| 4,688,780 A * | 8/1987 | Hanz | 5/621 |
| 5,092,050 A * | 3/1992 | Bardeen | 30/324 |
| 5,276,927 A | 1/1994 | Day | |
| 5,595,569 A * | 1/1997 | Hebbard | 606/131 |
| 5,697,164 A | 12/1997 | Hausmann et al. | |
| 5,782,244 A | 7/1998 | Kostich | |
| 5,947,981 A | 9/1999 | Cosman | |
| 6,101,650 A * | 8/2000 | Omdal et al. | 5/623 |
| 6,249,930 B1 * | 6/2001 | Noggle | 15/257.1 |
| D462,448 S | 9/2002 | Huttner | |
| 6,442,777 B1 | 9/2002 | Pauli | |
| 6,565,577 B2 | 5/2003 | Cosman | |
| 6,584,630 B1 | 7/2003 | Dinkler | |
| 6,662,036 B2 | 12/2003 | Cosman | |
| 6,892,419 B1 * | 5/2005 | Duprey | 15/257.9 |
| 6,898,810 B2 * | 5/2005 | Steven | 5/621 |
| 7,395,563 B2 | 7/2008 | Whitmore, III et al. | |
| 2003/0084512 A1 * | 5/2003 | Fujita et al. | 5/601 |
| 2009/0158526 A1 * | 6/2009 | Kinmon | 5/601 |

FOREIGN PATENT DOCUMENTS

| | | |
|---|---|---|
| JP | 2001198117 | 7/2001 |
| WO | WO 2006/034914 A1 | 4/2006 |
| WO | WO 2006/099841 A1 | 9/2006 |

* cited by examiner

*Primary Examiner* — Robert G Santos
(74) *Attorney, Agent, or Firm* — Carter, DeLuca, Farrell & Schmidt, LLP

(57) ABSTRACT

A patient support device for positioning the anatomy of a patient during a medical procedure includes a base and a handle. The base is supported on the top of a patient support table. The handle protrudes from a proximal side of the base. Both the base and the handle are made from a biocompatible, radiolucent material that is capable of being used during a radiographic procedure.

15 Claims, 5 Drawing Sheets

PATIENT SUPPORT DEVICE AND METHOD FOR USE

CROSS-REFERENCE TO RELATED APPLICATION

The present application claims priority to, and the benefit of, U.S. Provisional Patent Application Ser. No. 61/015,437, filed on Dec. 20, 2007, the entire contents of which are hereby incorporated by reference.

BACKGROUND

1. Technical Field

The present disclosure relates to a device, and method of use thereof, for stabilizing a portion of the human anatomy for procedures such as radiographic examinations and treatments. More specifically, the present disclosure relates to a device for providing support to the otherwise unsupported anatomy of a patient during examination and treatment.

2. Background of the Invention

Various diagnostic imaging technologies are known for visualization of internal organs and structures. Computed axial tomography (CAT), for example, is an x-ray scanning technique for producing cross-sectional images, while magnetic resonance imaging (MRI) is a radiation-free technique that uses a strong magnet and radiofrequency waves to produce images in desired "slice planes." During CAT and MR procedures in the clinical or operating room setting, a patient is placed on a movable support that translates within a housing. Traditional CAT and MRI equipment includes a ring-type gantry, and the patient is moved within the gantry so that images may be acquired of the anatomical region of interest. CAT is known to be particularly useful for volumetric imaging but also suffers from poor soft tissue contrast, while MRI offers multi-planar imaging with superior soft tissue contrast.

The use of CAT and MRI for intraoperative imaging and interventional radiology (e.g., performing minimally invasive, targeted treatments using imaging for guidance) previously has been limited because of the substantial challenges posed by the geometry and overall size of the imaging equipment. The donut-shaped, ring-type gantries of traditional CAT and MRI equipment, for example, are not easily accommodated, and can cause or suffer from various deleterious effects due to interactions with other equipment.

During the scanning procedure, the patient must maintain a perfectly still and motionless posture, and while most often, the patient simply lies on a scanning support table, in some situations, the patient may be supported in the desired scanning position with pads, straps or other supports. Further, the support table on which the patient rests is normally radiolucent, that is, transparent to the scanning device, so that the support does not compromise the utility of the scanned image. Further, the support table used for scanning normally translates with respect to the imaging device. Translation of the support table permits the patient to be moved into the scanning field or zone of the scanning machine.

The current support systems are generally a support table or structure that supports the entire patient as he or she is moved about the treatment facility, as illustrated in U.S. Pat. No. 6,584,630 to Whitmore et al. or a head support, as illustrated in U.S. Pat. No. 5,276,927 to Day. The head supports, as disclosed in Day, are generally expensive, directly attached to the support table, and complicated to use.

SUMMARY

A method and device for stabilizing portions of the human anatomy, such as limbs, is presently disclosed. The patient support device includes a base having a support structure protruding, e.g. handle, from the base. Both the base and the handle are made from a biocompatible, radiolucent material. Polypropylene homopolymer can be used as the biocompatible, radiolucent material. Materials such as glass fiber composite, carbon fiber composite, thermoset plastic, and thermoplastics can also be used to make the patient support device. The support device is generally light weight and can be quickly positioned, while minimizing the time and effort required by the operator.

In another embodiment, a patient support device, and method of use thereof, for stabilizing portions of the human anatomy and specifically the head, shoulders, and arms is disclosed. The patient support device has two support structures, or handles protruding from a base. The two handles are positioned on the base such that a patient's head can be located therebetween.

During use, the base of the patient support device is placed under the patient. The handles may be positioned above the patient's head or next to the patient's bead. The patient then engages the handles so that the arms and/or shoulders are at least partially supported by the handles providing stabilization of the region.

In this manner, the device can be used to stabilize the head, shoulders and/or limbs of the human body during certain medical procedures including X-rays, CT-scans, MRI, fluoroscopy, or nuclear camera and other radiographic procedures and therapeutic treatment of patients.

The patient is able to rest all or a portion of the weight of the anatomy on the device via the handles, allowing the patient to relax. The reduction in a patient's muscle tension during a procedure reduces movement and provides better results requiring less frequent re-examination. Additionally, this support minimizes the incidence of IV needles becoming dislodged during the procedure by allowing the patient's muscles to relax. As a result, the risk of potential harm to the patient is reduced.

In still another embodiment, the patient support device has adjustable handles and grips. The various embodiments and subcomponents may be provided in kits.

BRIEF DESCRIPTION OF THE DRAWINGS

Embodiments of the presently disclosed patient support device are disclosed herein with reference to the drawings wherein.

Figure 1:
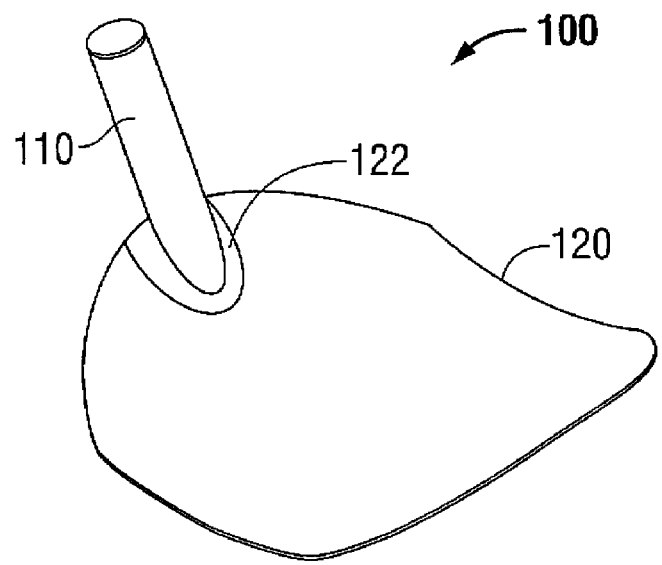
FIG. 1 is a perspective view of the patient support device in accordance with one embodiment of the present disclosure.
Figure 2:
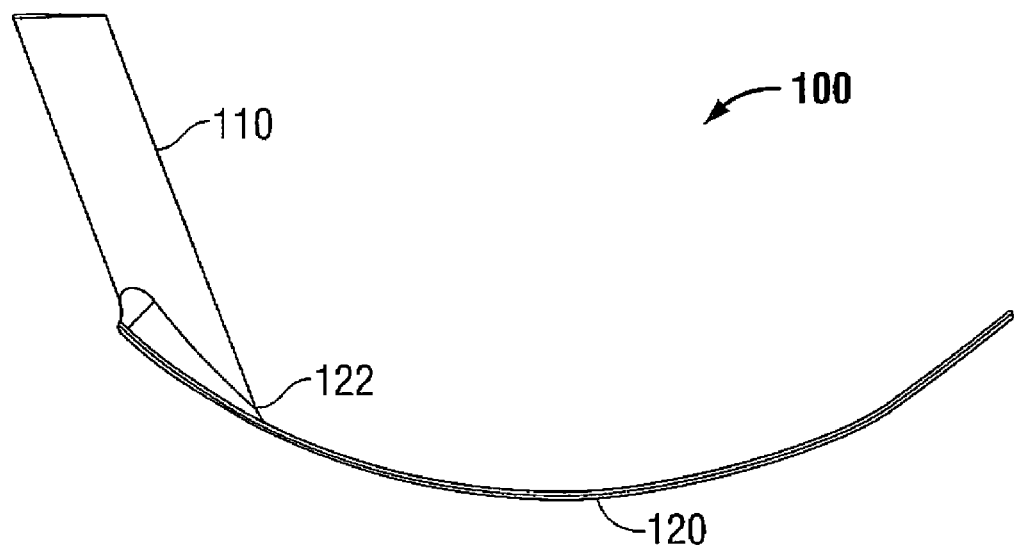
FIG. 2 is a front view of the patient support device in accordance with FIG. 1.
Figure 3:
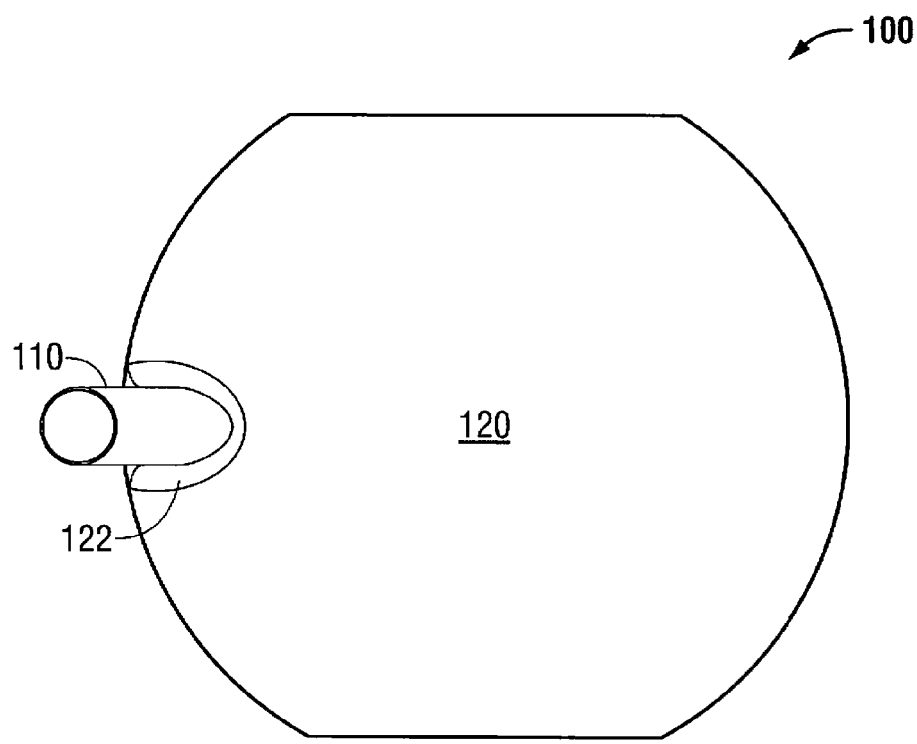
FIG. 3 is a top view of the patient support device in accordance with FIGS. 1 and 2.
Figure 4:
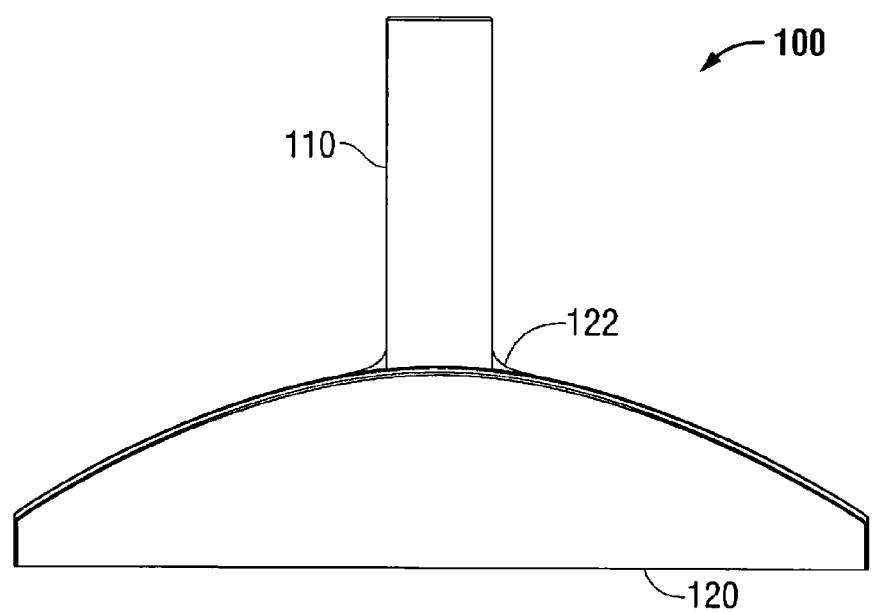
FIG. 4 is a side view of the patient support device in accordance with FIGS. 1-3.
Figure 5:
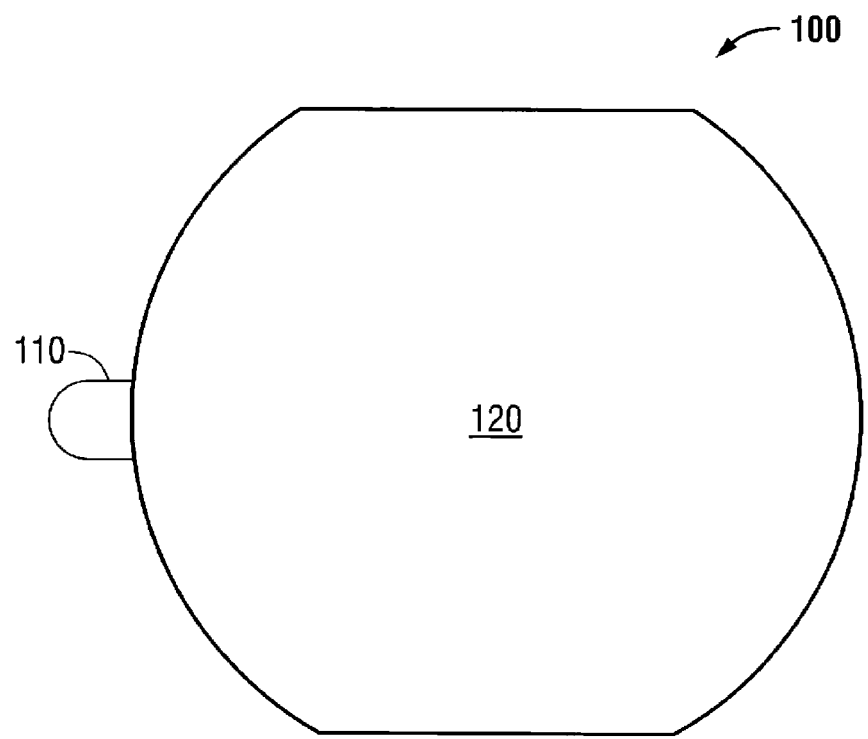
FIG. 5 is a bottom view of the patient support device in accordance with FIGS. 1-4.

Other features and advantages of the present disclosure will become apparent from the following detailed description, taken in conjunction with the accompanying drawings, which illustrate, by way of example, the principles of the present disclosure.

DETAILED DESCRIPTION OF THE EMBODIMENTS

Embodiments of the presently disclosed patient support device will now be described in detail with reference to the drawing figures, wherein like reference numerals identify identical or substantially similar parts throughout the several views. In the drawings and in the description which follows, the term "proximal", as is traditional, will refer to the end of the patient support device which is closest to the operator or patient, while the term "distal" will refer to the end of the device which is farthest from the operator or patient.

Referring now to the drawings, FIGS. 1-5 illustrate a patient support device that is generally designated as 100. The patient support device 100 includes a base 120 and a handle 110. The base 120 has a structural composition that allows it to conform with different contoured and uncontoured surfaces, including the patient's anatomy and/or diagnostic support tables. A fillet 122 provides a transition between the base 120 and the handle 110 to add strength, minimize retention of contaminants, and for ease of manufacture.

Both the base 120 and the handle 110 are a solid, monolithically formed structure made of a suitable biocompatible, radiolucent material that does not interfere with diagnostic imaging. This material may be plastic, composite, or other sterilizable medical material that provides for a solid, non-porous construction that can be easily sterilized. Glass fiber composites, carbon fiber composites, thermoset plastics, and thermoplastics can also be used to make the patient support device. A specific example of the material that can be used is polypropylene homopolymer. The patient support device may be formed by injection molding, blow molding, machining, lay-up, or a combination of these or other manufacturing process.

As a result, the patient support device 100 is a lightweight structure from which bodily fluids may be removed and be sterilized with a sterilizing agent, such as ethylene oxide, or by being placed in an autoclave. Once the patient support device 100 is sterilized, the patient support device 100 can be reused.

The base 120 is shaped to partially extend beneath the patient. The shape of the base 120 allows the base 120 to be inserted or slid between an patient support table and the patient without unduly disturbing the patient. Extending the base 120 partially under the patient provides additional stability to the base 120 by using the weight of the patient to counteract any moment applied through the handle 110.

A method for use of the patient support device 100 will now be discussed. In use, the patient or an operator slides the base 120 of the patient support device 100 between the patient and the surface of the diagnostic support table. The operator then places or instructs the patient to place the patient's anatomy in a certain position over the patient support device 100. The patient then at least partially relaxes the supporting muscular structure, transferring part of the weight of the positioned anatomy to the patient support device 100. A diagnostic examination is then done on the patient. Another similar, second patient support device 100, may also be slid under the patient from the other side of the table or bed, eliminating the need to raise the patient from the table, permitting the patient to support another portion of the patient's anatomy upon the second patient support device 100.

Figure 6:
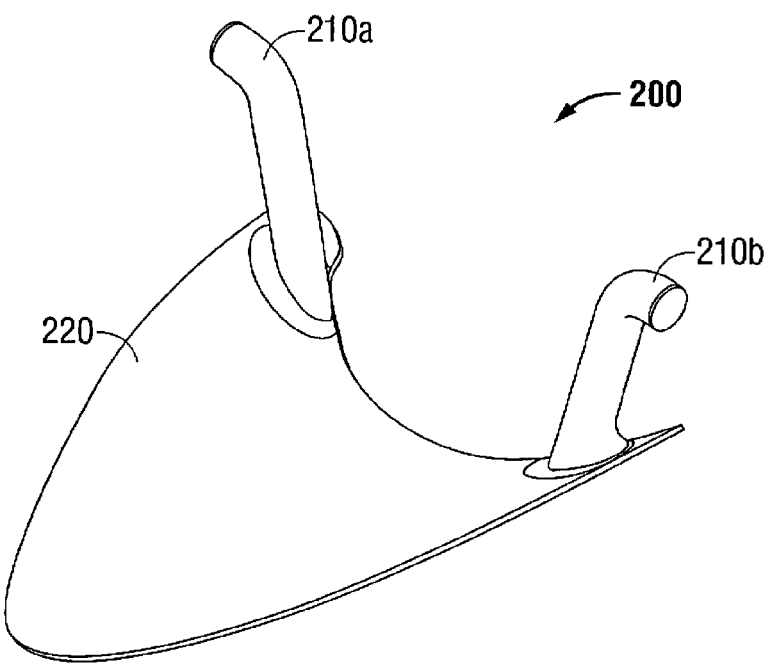
FIG. 6 is an isometric view of the patient support device in accordance with another embodiment of the present disclosure.
Figure 7:
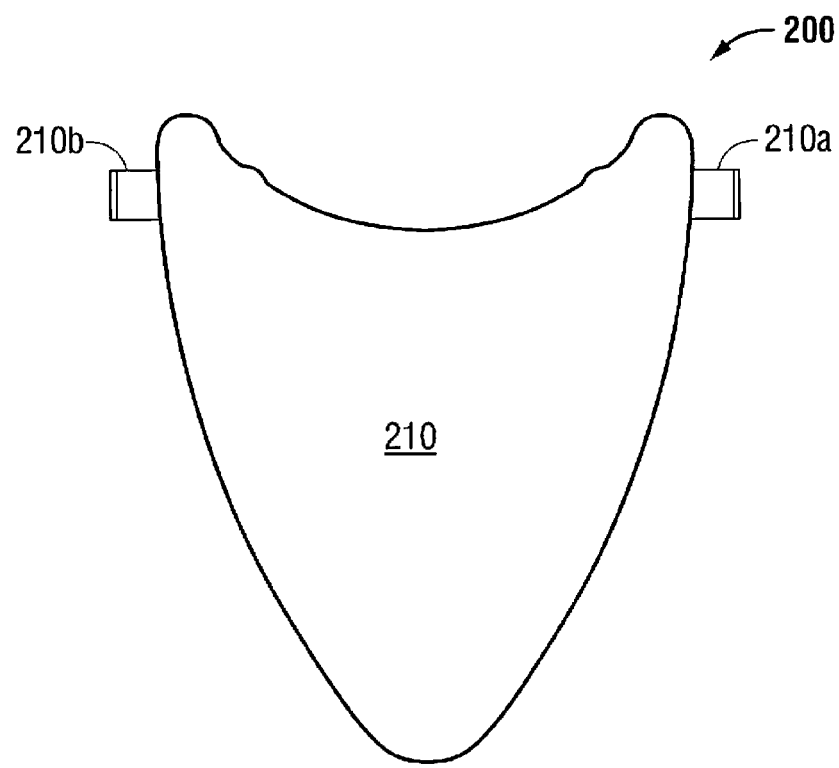
FIG. 7 is a bottom view of the patient support device in accordance with FIG. 6.

In another embodiment, the patient support device 200, as shown in FIGS. 6 and 7, includes a base 220 having a substantially a half conical shape and a first handle 210a and a second handle 210b. The shape of the base 220 allows the base 220 to slide under the patient's head and shoulders while minimally disturbing the patient. The first and second handles 210a, 210b are spaced far enough apart to allow a patient's head to be placed therebetween.

The base 220 and the first and second handles 210a, 210b are monolithically formed of a suitable biocompatible, radiolucent material that does not interfere with diagnostic imaging. Each of the first and second handles 210a, 210b has a curved section along the distal end to provide the patient and operator with multiple hand gripping positions.

In use, a patient's head and shoulders are placed on the base of the device. A clinician then places the handles 210a, 210b in a desired position relative to the patient's head. The desired position may be one of where the handles 210a, 210b are above or next to the patient's head. The patient grips the handles 210a, 210b so that the arms and/or shoulders are at least partially supported by the handles 210a, 210b to provide stabilization of the region. The base 220 of patient support device 200 rests on the examination bed, under the patient's head and shoulders.

The base of this embodiment provides stability to the head, shoulders, and arms; however, other shapes and sizes are envisioned for use with other body parts, and may include multiple handles that work simultaneously to support a single portion of anatomy.

Figure 8:
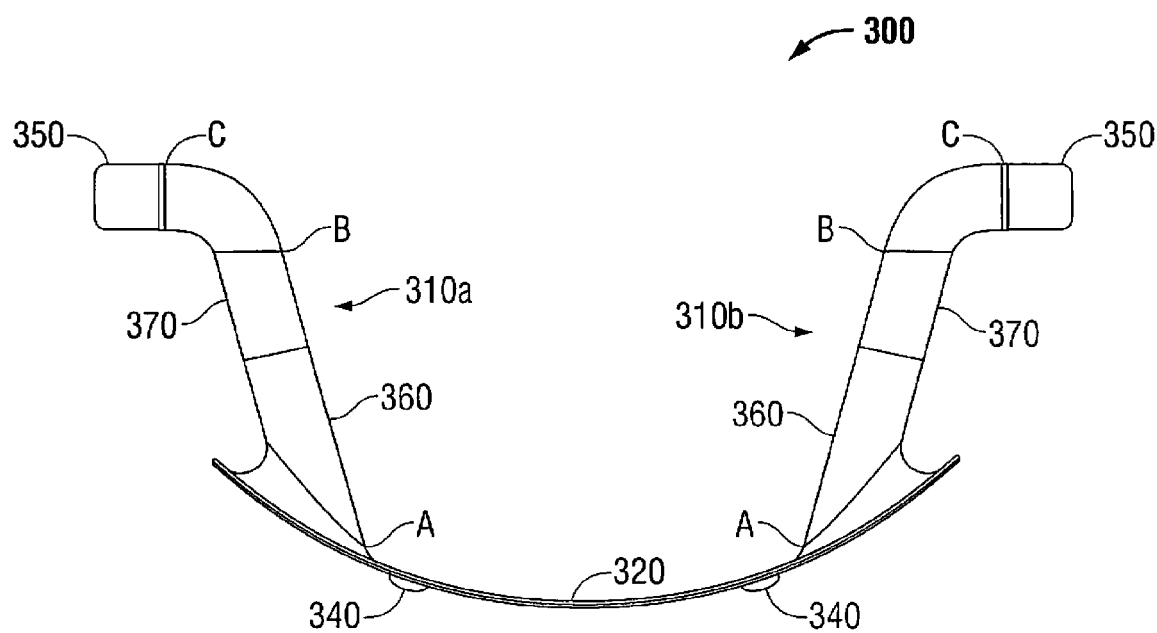
FIG. 8 is a front view of the patient support device in accordance with still another embodiment of the present disclosure.
Figure 9:
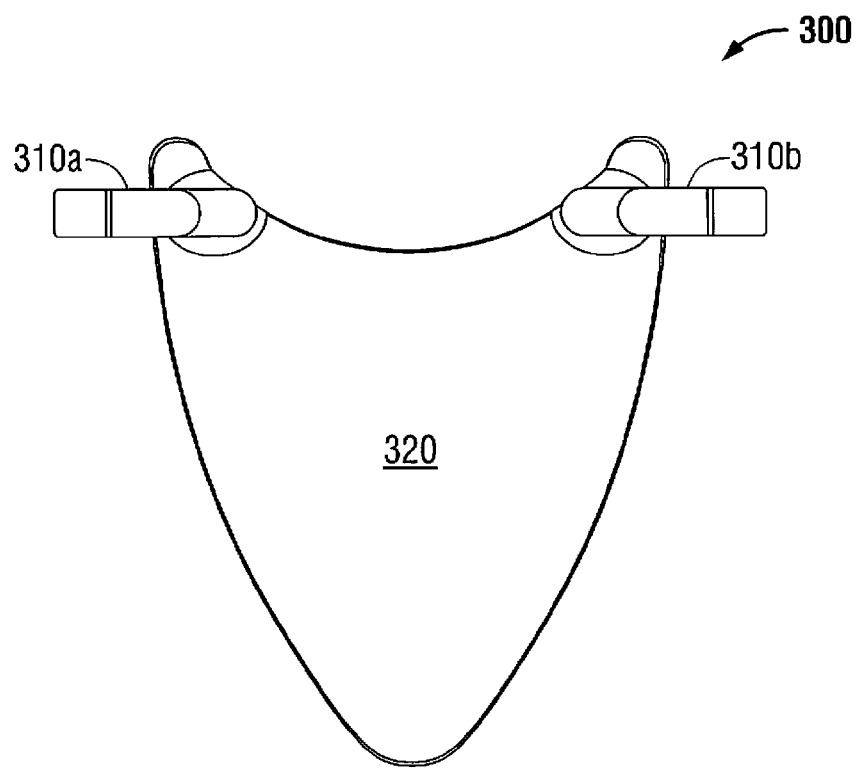
FIG. 9 is a top view of the patient support device in accordance with FIG. 8.
Figure 10:
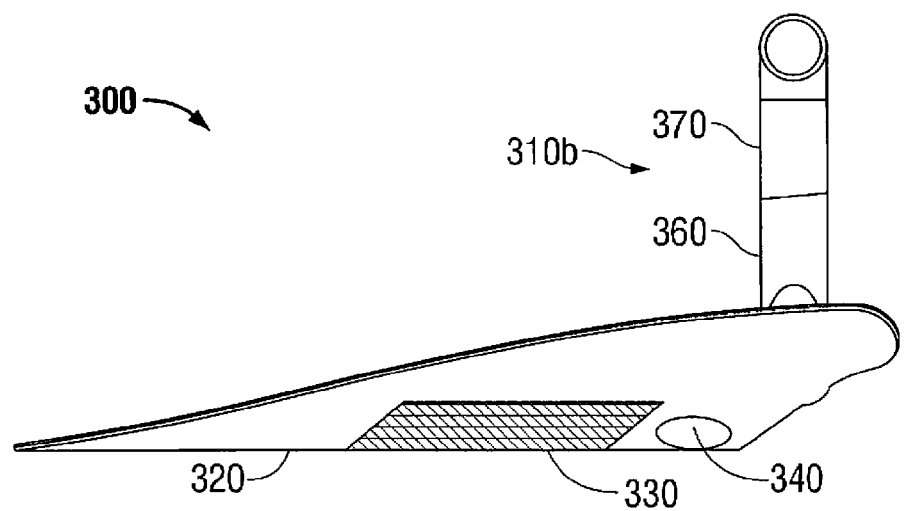
FIG. 10 is a side view of the patient support device in accordance with FIGS. 9 and 10.

In another embodiment, the patient support device 300, as shown in FIGS. 8-10, has abase 320 and a first handle 310a and a second handle 310b. Each of the 310a, 310b handle includes three parts namely: a lower handle section 360, an upper handle section 370, and a grip 350. Upper handle section 370 fits into or over the lower handle section 360 and provides the ability to vary the overall height of the grip 350 in relation to the base 320.

Various methods are envisioned to combine the upper and lower handles, such as screwing the upper and lower handle sections 360, 370 together and using a composite nut to lock the upper handle section 370 in place, a plastic locking pin to hold the upper and lower handle sections 360, 370 in place, or other fastening means. The grip 350 is also able to move inward or outward relative to the other handle by the same or different fastening mechanism. The grip 350 and upper handle section 370 may also be rotated about the lower handle section 360 to provide further angular/position variations.

The distal side of the base 320 has handles 310a, 310b on the inner or proximal surface that allow patients to comfortably support portions of the patient's anatomy. It is envisioned that each of the handles 310a, 310b pivotally rotate about points A, B, and C to obtain various configurations. Each point of rotation has several incremental angles to allow for maximum patient positioning.

The base 320 may include feet or stabilizing members 340 to provide additional stability. The feet may be constructed of foam, plastic or composite and may be removable and disposable. The underside of the base or distal side of the base 320, which is adjacent the examination table surface, may also be formed or coated or textured to form a non-skid surface 330 in order to limit unwanted shifting or sliding of the device during the examination process.

The grips 350 may be molded and adjusted to provide specific indexing of the hand. The grips 350 may also be shaped to support various other portions of anatomy during an examination procedure. The various shaped grips are interchangeable and replaceable. The handles may also be removed and replaced or repositioned upon the base.

While the device is shown as having a solid plastic construction, it is envisioned that memory foam can also be used for at least part of the device to better conform to the patient. Further, the device is disclosed as being sterilizable and reusable, however, it is envisioned that the device, or portion thereof, is inexpensive to manufacture and that the device may be used one time and then discarded. Still further, the base is shown as having a concave curvature; however, the base may also be convex, or substantially flat.

The patient support device may also be provided in kits. One envisioned kit provides a clinician with a multiplicity of different patient support devices, sized for patients of different sizes, and several grips configured to fit the different sized patient support devices. Another envisioned kit provides a single patient support device and several different grips designed to accept different body portions and patient sizes.

It is envisioned that the patient support device be used in surgical procedures. Since the patient support device is not being used in a diagnostic imaging device, the material can be radiopaque. Radiopaque metals such as aluminum, stainless steel, and titanium may be used. This short list of radiopaque materials is meant to be examples and is not meant to be limiting.

The patient support device may be used to "open" the chest during a procedure. The patient support device allows the patients arms to be supported overhead in a natural position to avoid damage to soft tissue. It is contemplated that a strap system or wrist supports be incorporated into the handles and/or base. This restraint system would provide the surgeon with the ability to hold the patient's limb or limbs in a derived position while the patient is unconscious.

It will be understood that various modifications may be made to the embodiments of the presently disclosed patient support device. By way of example only, the protrusion is a handle in the form of a straight cylinder; however, the protrusion could also take the form of a conformed grip or as a hook. Therefore, the above description should not be construed as limiting, but merely as exemplifications of embodiments. Those skilled in the art will envision other modifications within the scope and spirit of the present disclosure.

What is claimed is:

1. A patient support device comprising:
   a base including a material composition such that the base deforms during use in order to substantially conform to a portion of a patient's anatomy to provide supplemental anatomical support to the portion of the patient's anatomy in contact with the base during a medical procedure; and
   at least one handle extending outwardly from the base, and including a first, fixed end secured to the base, and a second, free end spaced from the first end, the handle having a length less than a width of the base and generally perpendicular to the width and length of the base, wherein the at least one handle extends outwardly from the base a distance sufficient to provide at least one surface configured and dimensioned for grasping by the patient during use of the patient support device, and the patient support device is made of a biocompatible and radiolucent material.

2. The patient support device of claim 1, wherein the base and the at least one handle are monolithically formed.

3. The patient support device of claim 1, wherein the base has a substantially half conical shape.

4. The patient support device of claim 1, wherein the patient support device is formed from a sterilizable medical material that is non-porous.

5. The patient support device of claim 1, wherein the material comprising the patient support device is selected from the group consisting of polypropylene homopolymer, glass fiber composite, carbon fiber composite, thermoplastic polymer, and thermoset plastic.

6. A patient support device comprising:
   a base including a material composition such that the base deforms during use in order to substantially conform to a portion of a patient's anatomy to provide supplemental anatomical support to the portion of the patient's anatomy in contact with the base during a medical procedure; and
   at least one handle extending outwardly from the base, the at least one handle including a first, fixed end secured to the base, and a second, free end spaced from the first end, the handle having a length less than a width of the base and generally perpendicular to the width and length of the base, wherein the at least one handle extends outwardly from the base a distance sufficient to provide at least one surface configured and dimensioned for grasping by the patient during use of the patient support device, and the base and the handle are monolithically formed from a biocompatible material.

7. The patient support device of claim 6, wherein the biocompatible material comprising the patient support device is radiolucent and is capable of being used during a radiographic procedure.

8. The patient support device of claim 7, wherein the biocompatible material comprising the patient support device is selected from the group consisting of polypropylene homopolymer, glass fiber composite, carbon fiber composite, thermoplastic polymer, and thermoset plastic.

9. The patient support device of claim 6, wherein the base has a substantially half conical shape.

10. The patient support device of claim 6, wherein the patient support device is formed from a sterilizable medical material that is non-porous.

11. The patient support device of claim 6, wherein the base is configured to be inserted under the patient by being slid between the patient and an examination surface supporting the patient.

12. The patient support device of claim 6, wherein the material comprising the patient support device is radiopaque and selected from the group consisting of aluminum, stainless steel, and titanium.

13. A patient support device comprising:
    a base including a material composition such that the base deforms during use in order to substantially conform to a portion of a patient's anatomy to provide supplemental anatomical support to the portion of the patient's anatomy in contact with the base during a medical procedure; and
    at least one handle secured to the base, the at least one handle extending outwardly from the base a distance sufficient to provide at least one surface configured and dimensioned for grasping by the patient during use of the patient support device, the handle having a length less than a width of the base and generally perpendicular to the width and length of the base.

14. The patient support device of claim 13, wherein the at least one handle includes a first, fixed end secured to the base, and a second, free end spaced from the first end.

15. The patient support device of claim 13, wherein the patient support device is made of a biocompatible and radiolucent material.

* * * * *